United States Patent [19]

Johnson

[11] Patent Number: 4,710,180
[45] Date of Patent: Dec. 1, 1987

[54] LIPOJECT NEEDLE

[76] Inventor: Gerald W. Johnson, 2010 Castlerock, Houston, Tex. 77090

[21] Appl. No.: 915,550

[22] Filed: Oct. 6, 1986

[51] Int. Cl.$^4$ ............................................. A61M 5/325
[52] U.S. Cl. ...................................... 604/239; 604/274
[58] Field of Search ............... 604/274, 239, 241, 272, 604/240, 218; 17/42.1

[56] References Cited

U.S. PATENT DOCUMENTS

| | | |
|---|---|---|
| D. 203,730 | 2/1966 | Goanda . |
| 561,059 | 5/1896 | Mitchell et al. ................ 604/239 X |
| 1,192,596 | 7/1916 | Albrecht ........................ 604/218 X |
| 2,097,039 | 10/1937 | Peterson . |
| 2,672,867 | 3/1954 | Ashkenaz .................... 604/241 |
| 2,836,942 | 6/1958 | Miskel . |
| 3,325,061 | 6/1967 | Ellsworth . |
| 3,994,295 | 1/1976 | Wulff . |
| 4,135,510 | 1/1979 | Assouly . |
| 4,190,048 | 2/1980 | Sampson . |
| 4,411,657 | 10/1983 | Galindo . |
| 4,413,993 | 11/1983 | Guttman ........................ 604/274 |
| 4,536,180 | 8/1985 | Johnson . |
| 4,537,593 | 8/1985 | Alchas . |
| 4,543,093 | 9/1985 | Christinger . |

FOREIGN PATENT DOCUMENTS 727847 4/1932 France ........................... 17/42.1
493203 9/1955 Italy ............................... 604/240

Primary Examiner—John D. Yasko
Attorney, Agent, or Firm—Laubscher & Laubscher

[57] ABSTRACT

A needle for atraumatic injection of particles of fat into the body of a patient is disclosed. The needle contains a through-bore which extends continuously between the proximal, intermediate, and distal portions thereof. The distal end of the needle has a generally conical configuration terminating in a relatively blunt, smooth surface. The needle is characterized by a plurality of radial ports equally spaced about the circumference of the intermediate portion adjacent the distal portion, and the cross-sectional area of each port corresponds with the cross-sectional area of the through-bore. When the needle is inserted into a given location below the skin of the body of a patient, and when particles of fat are delivered to the through-bore at the needle proximal portion, the particles are injected into the body via the ports.

8 Claims, 6 Drawing Figures

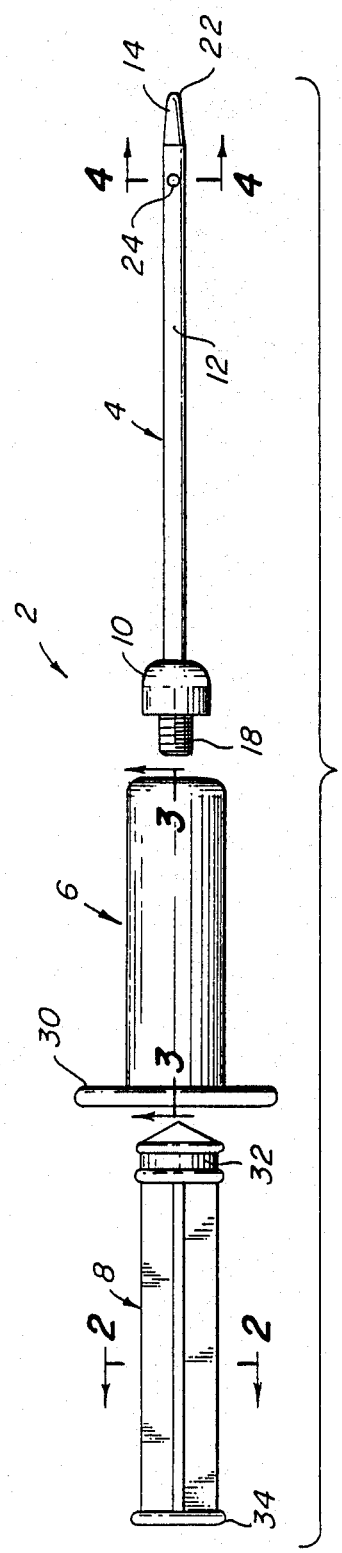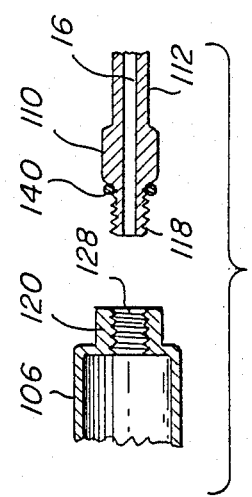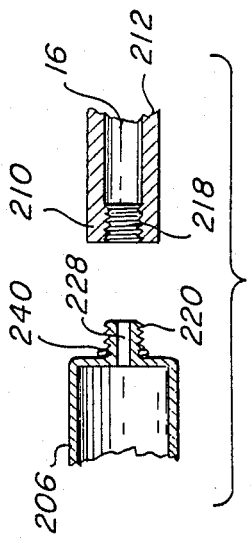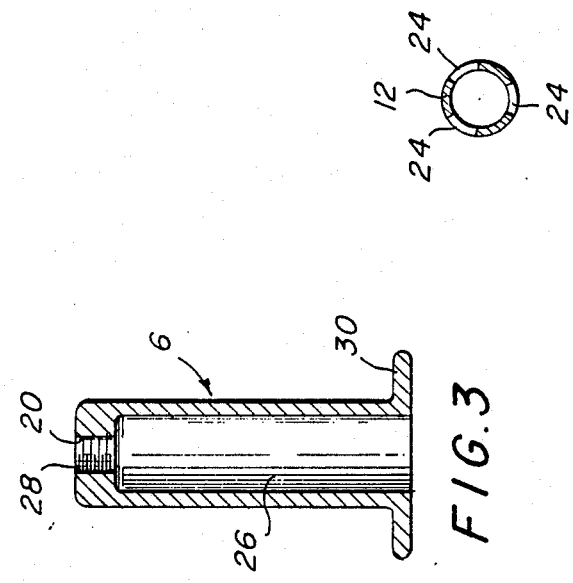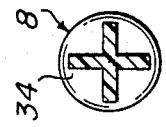

– 4,710,180 –

LIPOJECT NEEDLE

BACKGROUND OF THE INVENTION

In cosmetic and other types of surgery, it is often necessary to remove solid fat particles comprising living fat cells from one part of a patient's body and reinject them into another area of the body. The cells are normally removed by liposuction and retained in a sterile container. The cells are treated with a Heparin/Saline solution to separate the fat cells from blood and other body fluids which have also been removed by the liposuction process. Further cleansing of the fat cells with sterile physiologic saline prepares them for reinjection into the patient's body. The present invention relates to an improved needle for reinjection of the fat cells into a given location of the patient's body without penetrating a blood vessel.

BRIEF DESCRIPTION OF THE PRIOR ART

The inventor's prior U.S. Pat. No. 4,536,180 discloses a surgical instrument for liposuction. The instrument includes a long narrow tube having a pointed or tapered closed end which is inserted into a patient's body and an open end connected with a vacuum source. The tube is hollow and contains a side opening adjacent the closed end. When the closed end of the tube is inserted into an area of fatty deposits under a patient's skin and when the vacuum source is connected with the open end of the tube, fat cells are drawn through the side opening and the hollow passage within the tube for removal from the patient.

Needles for injection or aspiration of fluids relative to a patient's body are well known in the patented prior art, as evidenced by the Peterson U.S. Pat. No. 2,097,039, Sampson U.S. Pat. No. 4,190,048, Galindo U.S. Pat. No. 4,411,657, and Guttman U.S. Pat. No. 4,413,993. While these needles operate satisfactorily, they are generally designed with sharp points to allow the needle to penetrate a vein, whereas the present invention has been designed to prevent vein penetration. This is due to the fact that injection or entry of fat into veins can be fatal to the patient. Moreover, none of the prior needles are suitable for reinjection of particles of fat, which are larger and more solid than a liquid substance, into the body of a patient.

The present invention was developed to meet the need for a needle having a sufficiently large bore to allow for the passage of solid fat particles or cells without damaging or destroying them. The exit ports of the improved needle are located on the side of the needle shaft away from the needle tip and have a cross-sectional area equal to the cross-sectional area of the needle bore. This design enables particles of fat to be ejected from the needle without undue force in order to prevent traumatizing of the fat cells. Needles for the injection of liquids do not meet the criteria necessary for the injection of larger, denser fat cells.

SUMMARY OF THE INVENTION

Accordingly, it is a primary object of the present invention to provide an improved needle for atraumatic injection of particles of fat into the body of a patient. The elongated needle includes proximal, intermediate, and distal portions and contains a through-bore extending continuously between the proximal and distal portions. The intermediate portion of the needle has a generally tubular configuration, and the needle distal portion has a generally conical configuration, the remote end thereof having a blunt, smooth surface. The needle intermediate portion contains a plurality of radial ports equally spaced about the circumference of the intermedite portion adjacent the distal portion. The cross-sectional area of each port corresponds with the cross-sectional area of the through-bore. When the needle is inserted into a given location in the patient's body and when particles of fat are suppled to the proximal end of the needle through-bore, the particles are injected into the body via the ports.

According to another object of the invention, a syringe containing a quantity of fat particles is threadably connected with the proximal end of the needle.

It is yet another object of the invention to provide three ports arranged in the same cross-sectional area of the needle intermediate portion.

BRIEF DESCRIPTION OF THE FIGURES

Other objects and advantages of the subject invention will become apparent from a study of the following specification when viewed in the light of the accompanying drawing, in which:

FIG. 1 is an exploded plan view of the fat injection needle and syringe according to the invention;

FIG. 2 is a cross-sectional view of the syringe plunger taken along line 2—2 of FIG. 1;

FIG. 3 is a cross-sectional view of the syringe body member taken along line 3—3 of FIG. 1;

FIG. 4 is a cross-sectional view of the needle intermediate portion taken along line 4—4 of FIG. 1; and FIGS. 5 and 6 are partial sectional views of alternative threaded connections between the syringe and needle.

DETAILED DESCRIPTION

FIG. 1 illustrates the combination syringe and needle assembly 2 of the invention suitable for atraumatic injection of particles of fat into the body of a patient. The assembly includes a needle 4, a syringe body member 6, and a syringe plunger 8. The needle and syringe body member are formed of any suitable durable metal such as stainless steel and the syringe plunger is preferably formed of synthetic plastic material.

As shown in the drawing, the needle 4 is elongated and includes proximal 10, intermediate 12, and distal 14 portions. The needle also contains an elongated through-bore 16 which is shown more particularly in the cross-sectional view of the alternate embodiments of FIGS. 5 and 6. The through-bore extends continuously between the proximal and distal portions of the needle.

The intermediate portion 12 of the needle has a generally tubular configuration while the distal portion 14 has a conical configuration. As will be developed in greater detail below, the needle distal portion 14 may have any suitable configuration. In FIG. 1, the distal portion has a bell shape with a protruding threaded portion 18 adapted for threaded connection with the interior threads 20 of the syringe body shown in FIG. 3.

Referring once again to FIG. 1, the conically configured needle distal portion 14 terminates in a blunt smooth surface 22. Adjacent the distal portion 14, the needle intermediate portion 12 contains a plurality of radial ports 24 which communicate with the through-bore 16. As shown in FIG. 4, there are preferably three ports 24 which are equally spaced about the circumference of the needle intermediate portion 12. The ports each have a cross-sectional area equal to the cross-sectional area of the through-bore and are all arranged at the same cross-sectional area of the needle intermediate portion.

As shown in FIG. 3, the syringe body member 6 has a generally cylindrical configuration and contains a chamber 26 within which a quantity of particles of fat are arranged. The particles or cells of fat were previously removed from an area of the patient's body by a conventional liposuction technique and then cleaned to remove blood and other body fluids therefrom, with care being taken to preserve the cells in their living state. The inner threads 20 of the syringe body member 6 are arranged at one end thereof and surround an opening 28. The other end of the syringe body member is open and is surrounded by a flange 30 to facilitate operation of the syringe.

The plunger 8 is adapted for insertion into the open end of the syringe body member 6 and into the chamber 26. The forward end of the plunger has a flexible stopper 32 connected therewith. The stopper is preferably made of rubber and has an outer diameter slightly greater than the inner diameter of the chamber 26. The plunger is preferably fluted as shown in FIG. 2, with the height of each flute corresponding with the radius of the chamber. The plunger is adapted for sliding movement within the body member chamber and includes a knob 34 at its end opposite the stopper 32.

In operation, the needle 4 is threadably connected with the syringe body member 6 via the threaded portion 18 and the threads 20. A quantity of fat particles is arranged within the chamber 26 and the plunger 8 is partially inserted therein. An incision is made in the patient's skin at the location where the fat particles are to be injected. The distal portion 14 of the needle is inserted into the patient's body through the incision to the desired depth. Owing to the blunt, smooth surface 22 at the end of the needle distal portion, the needle does not penetrate any blood vessels during its insertion. Once the assembly is in place, the plunger is gradually slid into the chamber. Particles of fat pass from the chamber 26 via the opening 28 into the needle through bore 16. Further insertion of the plunger into the chamber causes the particles of fat to exit the needle through-bore via the ports 24 for even distribution throughout the injection site in the patient's body. Because the exit ports have the same cross-sectional area as the through-bore, no compression of cells results as they exit the needle. Thus, damage or trauma to the living fat cells is avoided.

Alternate configurations of the needle proximal portion are shown in FIGS. 5 and 6 for use in connection with syringes of different configurations. In FIG. 5, the syringe body member 106 includes an internally threaded protrusion 120 defining an opening 128. The needle distal portion 110 has an outer diameter greater than that of the needle intermediate portion 112. The distal portion contains a threaded portion 118 having a seal 140 such as an O-ring mounted thereon. When the needle and syringe body member are connected by the threaded portions 118, 120, the seal 140 is arranged between the needle distal portion and the syringe body member to prevent leakage of fat material. Of course, a similar seal could be provided for the threaded connection of the embodiment of FIG. 1.

In FIG. 6, the syringe body member 206 has an externally threaded protrusion 220 defining an opening 228 and having a seal 240 mounted thereon. The syringe distal portion 210 has the same outer diameter as the intermediate portion 212 and is internally threaded at 218 adjacent the bore 16 for connection with the syringe body member.

The technique and physiology of fat injection (or transcutaneous injection) has resulted from innovative ideas and methodology, from liposuction to remove fat, to the preparation of the fat cells for implantation, to the actual transcutaneous implantation of the fat in such a manner as to insure survival of the fat cells in their new location, as well as to provide proper contour for aesthetic reasons. The needle of the presention invention is an integral element of this entire process for which no other needle is sufficient.

While in accordance with the provisions of the patent statute the preferred forms and embodiments have been illustrated and described, it will be apparent to those skilled in the art that various changes may be made without deviating from the inventive concepts set forth above.

What is claimed is:

1. Apparatus for the atraumatic injection of particles of fat into the body of a patient, comprising
    an elongated needle having a successive proximal, intermediate, and distal portions and containing a through-bore extending continuously between said proximal and distal portions;
    said needle intermediate portion having a generally tubular configuration;
    said needle distal portion having a generally conical configuration, the remote end thereof having a blunt smooth surface;
    said needle intermediate portion containing a plurality of radial ports equally spaced about the circumference thereof adjacent said distal portion, the cross-sectional area of each of said ports corresponding with the cross-sectional area of said through-bore, whereby when said needle distal and intermediate portion are inserted into a given location in the body of a patient and when particles of fat are supplied to the proximal end of said needle through-bore, the particles are injected into the body via said ports.

2. Apparatus as defined in claim 1, wherein said ports are contained in a single cross-sectional area of said needle intermediate portion.

3. Apparatus as defined in claim 2, and further comprising a syringe connected with said needle proximal portion, said syringe containing a quantity of particles of fat.

4. Apparatus as defined in claim 3, wherein said syringe comprises
    (a) a generally cylindrical body member containing a chamber for receiving the particles of fat, said body member being open at one end and containing a connection opening at the other end thereof for connection with said needle and affording communication between said body member chamber and said needle throug-bore; and
    (b) a plunger slidably mounted within said chamber, said plunger including a flexible stopper connected with the forward portion thereof, the outer diameter of said stopper being slightly greater than the inner diameter of said chamber, whereby when said plunger is inserted into said chamber, the particles of fat are ejected out of said chamber via said connection opening and into the body of a patient via said needle through-bore and ports, respectively.

5. Apparatus as defined in claim 4, and further comprising sealing means arranged between said needle and syringe.

6. Apparatus as defined in claim 5, wherein said needle and said syringe body member are formed of metal, and further wherein said plunger stopper is formed of rubber material.

7. Apparatus as defined in claim 6, wherein three ports are provided in said needle intermediate portion.

8. Apparatus is defined in claim 7, wherein said syringe is threadably connected with said needle proximal portion.

* * * * *